(12) United States Patent
Kuegler et al.

(10) Patent No.: US 8,766,251 B2
(45) Date of Patent: Jul. 1, 2014

(54) FUNCTIONAL MATERIAL FOR PRINTED ELECTRONIC COMPONENTS

(75) Inventors: Ralf Kuegler, Cambridge, MA (US); Andreas Klyszcz, Darmstadt (DE); Sabine Renker, Limburg (DE); Joerg J. Schneider, Seeheim-Jugenheim (DE); Rudolf Hoffmann, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 149 days.

(21) Appl. No.: 13/143,837

(22) PCT Filed: Dec. 10, 2009

(86) PCT No.: PCT/EP2009/008821
§ 371 (c)(1),
(2), (4) Date: Jul. 8, 2011

(87) PCT Pub. No.: WO2010/078907
PCT Pub. Date: Jul. 15, 2010

(65) Prior Publication Data
US 2011/0272691 A1    Nov. 10, 2011

(30) Foreign Application Priority Data
Jan. 9, 2009   (DE) .......................... 10 2009 004 491

(51) Int. Cl.
*H01L 29/10* (2006.01)
*H01L 29/786* (2006.01)
*H01L 21/02* (2006.01)

(52) U.S. Cl.
CPC ........ *H01L 29/786* (2013.01); *H01L 21/02288* (2013.01)
USPC ........................................................ 257/43

(58) Field of Classification Search
CPC .................... H01L 21/02288; H01L 29/786
USPC ................ 257/40, 43, 72, E33.064, E31.126
See application file for complete search history.

(56) References Cited

U.S. PATENT DOCUMENTS

| 2005/0199880 A1* | 9/2005 | Hoffman et al. ................. 257/72 |
| 2005/0199959 A1* | 9/2005 | Chiang et al. ................. 257/368 |
| 2009/0146138 A1* | 6/2009 | Aoki .............................. 257/40 |

FOREIGN PATENT DOCUMENTS

| JP | 63-162673 A | 7/1988 |
| WO | WO 2009/010142 A2 | 1/2009 |

OTHER PUBLICATIONS

International Search Report of PCT/EP2009/008821 (Mar. 22, 2010).
A. Moses et al., "Spray Pyrolysis Deposition and Characterization of Highly (100) Oriented Magnesium Oxide Thin Films", Cryst. Res. Technol., vol. 42, No. 9 (2007) pp. 867-875.
K. V. Zherikova et al., "Thermal Properties of Hafnium(IV) and Zirconium(IV) Beta-Diketonates", Journal of Thermal Analysis and Calorimetry, vol. 92, No. 3 (2008) pp. 729-734.

(Continued)

*Primary Examiner* — Brook Kebede
(74) *Attorney, Agent, or Firm* — Millen, White, Zelano & Branigan, P.C.

(57) ABSTRACT

The invention relates to a printable precursor comprising an organometallic aluminum, gallium, neodymium, ruthenium, magnesium, hafnium, zirconium, indium and/or tin complex or a mixture thereof which contains at least one ligand from the class of the oximates, for electronic components, and to a preparation process. The invention furthermore relates to corresponding printed electronic components, preferably field-effect transistors.

21 Claims, 8 Drawing Sheets

(56) References Cited

OTHER PUBLICATIONS

H. M. Ismail, "Characterization of the Decomposition Products of Zirconium Acetylacetonate: Nitrogen Adsorption and Spectrothermal Investigation", Powder Technology, vol. 85 (1995) pp. 253-259.

O. Stryckmans et al., "Formation of Mg0 Films by Ultrasonic Spray Pyrolysis from Beta-Diketonate", Thin Solid Films, vol. 283 (1996) pp. 17-25.

M. R. Hill et al., "Towards New Precursors for ZnO Thin Films by Single Source CVD: The X-Ray Structures and Precursor Properties of Zinc Ketoacidoximates", Inorganica Chimica Acta, vol. 358 (2005) pp. 201-206.

A. Apblett et al., "Incorporation of Radionuclides into Mineral Phases via a Thermally Unstable Complexant Ligand", Database CA, Chemical Abstracts Service, XP002574350, Materials Research Society Symposium Proceedings, vol. 294 (1993) pp. 123-128.

S. Kojima et al., "Preparation of Iminoacetic Acid Derivatives as Fungicides", Database CA, Chemical Abstracts Service, XP002574351.

YTH Translation of JP (B2) 2556317.

* cited by examiner

FUNCTIONAL MATERIAL FOR PRINTED ELECTRONIC COMPONENTS

The invention relates to an aluminium-, gallium-, neodymium-, ruthenium-, magnesium-, hafnium-, zirconium-, indium- and/or tin-containing precursor for electronic components and to a preparation process. Furthermore, the invention relates to corresponding printed electronic components and to production processes which are suitable for these.

For use of printed electronics in mass applications (for example RFID (=radio frequency identification) chips on individual packages), the use of established mass printing processes is desirable. In general, printed electronic components and systems consist of a plurality of material components, such as conductors for, for example, contacts, semiconductors, for example as active materials, and insulators, for example as barrier layers.

The production processes usually consist of a deposition step, i.e. the application of the respective material to a support material (substrate), and a subsequent process step, which ensures the desired properties of the material. With respect to suitability for mass, for example roll-to-roll, processing, the use of flexible substrates (films or foils) is desirable. Previous processes for the production of printed circuits have intrinsic advantages, but also disadvantages:

Conventional technology (see WO 2004086289): Here, hybrids of conventional Si logic units and additional structured or printed components (for example metal antenna in the case of an RFID chip) are assembled in a cost-intensive manner. However, this process is regarded as too complex for the purposes of an actual volume application.

Organic materials (see DE 19851703, WO 2004063806, WO 2002015264): These systems are printed electronic components based on polymers from the liquid phase. These systems are distinguished by simple processing from solutions compared with the previously known materials (conventional technology). The only process step to be taken into account here is drying of the solvent. However, the achievable efficiency in the case of, for example, semiconducting or conducting materials is restricted by limiting material-typical properties, such as, for example, the charge-carrier mobility <10 cm$^2$/Vs due to so-called hopping mechanisms. This restriction affects the applicational possibilities: the efficiency of a printed transistor increases with reduced dimension of the semiconducting channel, which cannot at present be printed smaller than ~40 μm using mass processes. A further restriction of the technology is the sensitivity of the organic components to ambient conditions. This complicates performance of the process during production and possibly results in a shortened lifetime of the printed components.

Inorganic materials: due to different intrinsic properties (for example stability to UV-induced degradation) compared with the organic materials, this class of materials generally has the potential for increased efficiency on use in printed electronics.

In principle, two different approaches can be used in this area:

i) Preparation from the gas phase without an additional process step: in this case, it is possible to produce thin layers which insulate very well, but the associated cost-intensive vacuum technology and the slow layer growth limit use in the mass market.

ii) Wet-chemical preparation starting from precursor materials, where the materials are applied from the liquid phase, for example by spin coating or printing (see U.S. Pat. No. 6,867,081, U.S. Pat. No. 6,867,422, US 2005/0009225). In some cases, mixtures of inorganic materials and an organic matrix are also used (see US 2006/0014365).

In order to guarantee an electrical property throughout the layer produced, a process step which goes beyond evaporation of the solvent is usually necessary. In all cases, it is necessary to produce a morphology with regions which run into one another, where precursors from the wet phase are additionally converted into the desired active material. This produces a desired functionality (in the case of semiconductors: high charge-carrier mobility). The processing is therefore carried out at temperatures >300° C., but this prevents use of this process for film coating.

Examples of the use of a precursor material for MgO are described, for example, in Stryckmans et al. Thin Solid Films 1996, 283, 17 (from magnesium acetylacetonate above 260° C.) or Raj et al. Crystal Research and Technology 2007, 42, 867 (from magnesium acetate from 300° C. in a number of steps). In both cases, spray pyrolysis is employed for layer deposition from the gas phase. In this case, the solutions are sprayed onto a heated substrate (above 400° C.) and optionally aftertreated at even higher temperature. The high temperatures necessary prevent use in printing processes.

An example of the use of a soluble $ZrO_2$ precursor material is described in Ismail et al. Powder Technology 1995, 85, 253 (from zirconium acetyl-acetonate over a number of hours at between 200 and 600° C.).

An example of the use of a soluble $HfO_2$ is known, for example, from Zherikova et al. Journal of Thermal Analysis and Calorimetry 2008, 92, 729 (from hafnium acetylacetonate over a number of hours at between T=150 and 500° C.).

beta-Diketonates, such as the acetylacetonates of zirconium and hafnium, are employed in layer deposition from the gas phase by means of chemical vapour deposition (CVD). Here, the compounds are evaporated in a high vacuum and deposited on heated substrates (above 500° C.). The conversion to the oxidic ceramic is carried out via a number of discrete intermediates, although these are not used as functional material. High temperatures which guarantee a defined reaction are thus necessary, which prevents use in printing processes.

For the preparation of indium tin oxide (abbreviated to "ITO"), the precursors used are, for example, sols of tin and indium salts in the presence of amines, such as ethanolamine (Prodi et al. Journal of Sol-Gel Science and Technology 2008, 47, 68). The conversion to the oxide is carried out here at temperatures above 500-600° C. The high temperatures necessary prevent use in printing processes on temperature-sensitive substrates.

The preparation of amorphous, semiconducting oxide ceramics is of interest (K. Nomura et al. Nature 2004, 432, 488-492; H. Hosono Journal of Non-Crystalline Solids 2006, 352, 851-858; T. Kamiya et al. Journal of Display Technology 2009, 5, 273-288). The indium-gallium-tin-zinc-oxygen phase system has been investigated in detail here. Typical examples are indium gallium zinc oxide (abbreviated to "IGZO"), and zinc tin oxide (abbreviated to "ZTO"), but also indium zinc tin oxide (abbreviated to "IZTO").

The deposition of semiconducting layers is usually carried out via the gas phase, but processes based on solutions are also known. However, the sols employed here make relatively high processing temperatures necessary. Zinc tin oxide can be obtained from anhydrous tin(II) chloride or tin(II) acetate and zinc acetate hexahydrate in the presence of bases, such as ethanolamine. The conversion to the oxide (with oxidation of the tin components) is carried out at least 350° C. (D. Kim et al. Langmuir 2009, 25, 11149-11154) or 400-500° C. (S. J. Seo et al. Journal of Physics D: Applied Physics, 2009, 42, 035106), depending on the reaction performance during calcination, in air. Indium zinc tin oxide is obtained from anhydrous indium chloride, zinc chloride and tin(II) chloride in ethylene glycol by reaction with sodium hydroxide solution and subsequent calcination at 600° C. (D. H. Lee et al. Journal of Materials Chemistry 2009, 19, 3135-3137).

The use of these conventional precursors for the production of printed circuits is restricted in its applicability in volume production of a mass-printing application.

The object of the present invention was therefore to provide inorganic materials whose dielectric, semiconducting and conducting properties can be adjusted on the one hand through the material composition and on the other hand through the preparation process of the printed materials. To this end, the aim is to develop material systems which retain the advantages of inorganic materials. It should be possible to process the material from the wet phase by a printing process. The electronic efficiency of the material desired in each case on planar and flexible substrates should be produced using a process step which requires only low input of energy.

Surprisingly, a process has now been developed in which a novel organometallic precursor material is prepared, applied to surfaces and subsequently converted at low temperatures into a dielectrically active, i.e. insulating, material and also into an electrically semiconducting or conducting material. The layers produced in the process are distinguished by surface properties which are advantageous for a printing process.

The present invention thus relates to a precursor for the coating of electronic components, characterised in that it comprises an organometallic aluminium, gallium, neodymium, ruthenium, magnesium, hafnium, zirconium, indium and/or tin complex or a mixture thereof which contains at least one ligand from the class of the oximates.

If the reaction is performed in a suitable way, the precursors can also be prepared alkali metal-free. This may be advantageous for use in electronic components since alkali metal-containing residues can have an adverse effect on the electronic properties. These elements, as foreign atoms in the crystal, can have an unfavourable influence on the properties.

In a preferred embodiment, the precursor is printable and is in the form of a printing ink or printing paste for the coating of printed field-effect transistors (FETs), preferably thin-film transistors (TFTs).

The term "printable precursor" is taken to mean a precursor material which, owing to its material properties, can be processed from the wet phase by a printing process. During the printing process, a printing ink or printing paste is transported from a stock container to a substrate depending on the printing process.

The precursor material must therefore be capable of conversion into a printing ink or printing paste of this type which has a viscosity and stability during the printing process which are suitable for the printing process, and has suitable wettability and adhesion to the substrate.

Experience shows that different viscosity ranges of the ink or paste are preferred for different printing processes; for example 1-5 mPa·s for ink-jet printing (thermal), 5-20 mPa·s for ink-jet printing (piezoelectric), 50-200 mPa·s for gravure printing, 50-500 mPa·s for flexographic printing and 2000-40,000 mPa·s for screen printing.

As already described above, the precursor comprises an organometallic aluminium, gallium, neodymium, ruthenium, magnesium, hafnium, zirconium, indium and/or tin complex having at least one ligand from the class of the oximates. It is preferred in accordance with the invention for the ligands of the aluminium, gallium, neodymium, ruthenium, magnesium, hafnium, zirconium, indium and/or tin complex to contain a 2-(methoxyimino)alkanoate, 2-(ethoxyimino)alkanoate or 2-(hydroxyimino)alkanoate. The ligands are synthesised by condensation of alpha-keto acids or oxocarboxylic acids with hydroxylamines or alkylhydroxylamines in the presence of bases in aqueous or methanolic solution.

The precursors or aluminium, gallium, neodymium, ruthenium, magnesium, hafnium, zirconium, indium and/or tin complexes form at room temperature by reaction of an oxocarboxylic acid with at least one hydroxylamine or alkylhydroxylamine in the presence of a base, such as, for example, tetra-ethylammonium hydrogencarbonate or sodium hydrogencarbonate, and subsequent addition of an inorganic aluminium, gallium, neodymium, ruthenium, magnesium, hafnium, zirconium, indium and/or tin salt, such as, for example, aluminium nitrate nonahydrate, gallium nitrate hexahydrate, anhydrous neodymium trichloride, ruthenium trichloride hexahydrate, magnesium nitrate hexahydrate, zirconium oxochloride octahydrate, hafnium oxochloride octahydrate, anhydrous indium chloride and/or tin chloride pentahydrate. Alternatively, an oxocarboxylic acid can be reacted with a hydroxocarbonate of magnesium, hafnium or zirconium, such as, for example, hydromagnesite $Mg_5(CO_3)_4(OH)_2 \cdot 4H_2O$, in the presence of at least one hydroxylamine or alkylhydroxylamine.

Oxocarboxylic acids which can be employed are all representatives of this class of compounds. However, preference is given to the use of oxoacetic acid, oxopropionic acid or oxobutyric acid.

The thermal conversion of the aluminium, gallium, neodymium, magnesium, hafnium or zirconium complex precursor into the functional aluminium oxide, gallium oxide, neodymium oxide, magnesium oxide, hafnium oxide or zirconium oxide layer having insulating properties or of the ruthenium complex precursor into a layer of ruthenium oxide is carried out at a temperature ≥80° C. The temperature is preferably between 150 and 200° C. The thermal conversion of the indium and tin complex precursors into the functional indium tin oxide layer having conducting properties is carried out at a temperature ≥150° C. The temperature is preferably between 150 and 250° C.

The thermal conversion of the indium, gallium and zinc complex precursors into the functional indium gallium zinc oxide layer having semiconducting properties is carried out at a temperature ≥150° C. The temperature is preferably between 150 and 250° C.

The thermal conversion of the zinc and tin complex precursors into the functional zinc tin oxide layer having semiconducting properties is carried out at a temperature ≥150° C. The temperature is preferably between 150 and 250° C.

The conversion of the aluminium, gallium, neodymium, magnesium, hafnium or zirconium complex precursor into the functional aluminium, gallium, magnesium, hafnium or zirconium oxide layer having insulating properties or the conversion of the ruthenium complex precursor into ruthenium oxide or the conversion of the indium and tin complex precursors into the functional indium tin oxide layer having conducting properties or the conversion of the indium-gallium-zinc and tin complex precursors into the functional oxide layer having semiconducting properties is carried out in a further preferred embodiment by irradiation with UV light having wavelengths <400 nm. The wavelength is preferably between 150 and 380 nm. The advantage in the case of UV irradiation is that the aluminium oxide, gallium oxide, neodymium oxide, ruthenium oxide, magnesium oxide, hafnium oxide, zirconium oxide, indium tin oxide and indium gallium zinc oxide or zinc tin oxide layers produced thereby have lower surface roughness. This is because increased roughness of the surfaces would mean, for the thin subsequent layers, an increased risk of these layers not being able to form homogeneously and thus not being electrically functional (for example short circuit due to a damaged dielectric layer).

Aluminium oxide, gallium oxide, neodymium oxide, magnesium oxide, hafnium oxide or zirconium oxide layers produced from the corresponding precursors exhibit a breakdown voltage of >0.1 MV/cm between two conductors. Preference is given to breakdown voltages of between 1 and 10 MV/cm.

The breakdown voltage can be determined by means of the measurement and evaluation methods described in DIN EN ISO 2376:2009-07.

The indium tin oxide layer (ITO layer) preferably has a specific resistance (determined by four-point measurement) of $<10^{-3}$ ohm·cm. Specific resistances of between $10^{-3}$ and $10^{-5}$ ohm·cm are preferred.

The conductivity can be determined by means of a four-probe direct-current method. This measurement method is described in DIN 50431 or ASTM F43-99.

The indium gallium zinc oxide (IGZO) layers or the zinc tin oxide (ZTO) layers preferably have a charge-carrier mobility of $>10^{-3}$ cm$^2$/Vs. Preference is given to charge-carrier mobilities of 0.1 to 10 cm$^2$/Vs.

The characterisation and determination of parameters of semiconducting materials can be carried out by means of the measurement and evaluation methods described in IEEE 1620.

The present invention furthermore relates to the use of the organometallic aluminium, gallium, neodymium, ruthenium, magnesium, hafnium, zirconium, indium and/or tin complex or precursor according to the invention for the production of one or more functional layers in a field-effect transistor.

In accordance with the invention, the substrate can be either a solid substrate, such as glass, ceramic, metal or a plastic substrate, or a flexible substrate, in particular plastic film or metal foil. In accordance with the invention, a flexible substrate (film or foil) is preferably employed.

The application of the precursor solutions according to the invention to the substrate by methods such as dip coating, spin coating and ink-jet printing or flexographic/gravure printing is known to the person skilled in the art (see M. A. Aegerter, M. Menning; Sol-Gel Technologies for Glass Producers and Users, Kluwer Academic Publishers, Dordrecht, Netherlands, 2004), where ink-jet printing or flexographic/gravure printing is preferred in accordance with the invention.

The term "field-effect transistor (FET)" is taken to mean a group of unipolar transistors in which, in contrast to bipolar transistors, only one charge type is involved in current transport—electrons or holes or defect electrons, depending on the design. The most widespread type of FET is the MOSFET (metal oxide semiconductor FET).

The FET has three connections:
source
gate
drain.

In the MOSFET, a fourth bulk (substrate) connection is also present. In the case of individual transistors, this is already internally connected to the source connection and is not connected separately.

In accordance with the invention, the term "FET" generally encompasses the following types of field-effect transistor:
barrier-layer field-effect transistor (JFET)
Schottky field-effect transistor (MESFET)
metal oxide semiconductor FET (MOSFET)
high electron mobility transistor (HEMT)
ion-sensitive field-effect transistor (ISFET)
thin-film transistor (TFT).

Preference is given in accordance with the invention to the TFT, by means of which large-area electronic circuits can be produced.

The present invention furthermore relates to a printed electronic component which has the following thin layers:
a solid or flexible, conductive substrate or an insulating substrate having a conductive layer (gate)
an insulator comprising an aluminium, gallium, neodymium, magnesium, hafnium or zirconium oxide obtainable from the corresponding precursor, the organometallic aluminium, gallium, neodymium, magnesium, hafnium or zirconium complex, which contains at least one ligand from the class of the oximates
at least one electrode (drain electrode)
a semiconductor.

The aluminium, gallium, neodymium, magnesium, hafnium or zirconium oxide layer has a thickness of 15 nm to 1 µm, preferably 30 nm to 750 nm. The layer thickness is dependent on the coating technique used in each case and its parameters. In the case of spin coating, these are, for example, the speed and duration of rotation.

The present invention furthermore relates to a printed electronic component which has the following thin layers:
a solid or flexible, conductive substrate or an insulating substrate having a conductive layer (gate) comprising an indium tin oxide (ITO) obtainable from the corresponding precursors, organometallic indium and tin complexes, which contain at least one ligand from the class of the oximates
an insulator
at least one electrode (drain electrode)
a semiconductor.

The indium tin oxide layer (ITO layer) has a thickness of 15 nm to 1 µm, preferably 100 nm to 500 nm. The layer thickness is dependent on the coating technique used in each case and its parameters. In the case of spin coating, these are, for example, the speed and duration of rotation.

The present invention furthermore relates to a printed electronic component which has the following thin layers:
a solid or flexible, conductive substrate or an insulating substrate having a conductive layer (gate)
an insulator
at least one electrode (drain electrode)
a semiconductor. The semiconductor should consist of a multinary, amorphous phase comprising indium gallium zinc oxide (IGZO) or alternatively zinc tin oxide (ZTO), obtainable from the corresponding precursors, the organometallic indium, gallium, zinc complexes or the zinc and tin complexes, which contain at least one ligand from the class of the oximates.

The indium gallium zinc oxide (IGZO) or zinc tin oxide (ZTO) layer has a thickness of 15 nm to 1 µm, preferably 20 nm to 200 nm. The layer thickness is dependent on the coating technique used in each case and its parameters. In the case of spin coating, these are, for example, the speed and duration of rotation.

In a preferred embodiment, the electronic components mentioned above consist of a field-effect transistor or thin-film transistor which is built up from a gate, an insulating layer, a semiconductor and electrodes (drain and source). The gate preferably consists of a highly n-doped silicon wafer, a highly n-doped silicon thin layer, conductive polymers (for example polypyrrole-polyaminobenzenesulfonic acid or polyethylenedioxythiophene-polystyrenesulfonic acid (PE- DOT-PSS)), conductive ceramics (for example indium tin oxide (ITO) or Al-, Ga- or In-doped tin oxide (AZO, GZO, IZO) and F- or Sb-doped tin oxide (FTO, ATO)) or metals (for example gold, silver, titanium, zinc), depending on the design as a thin layer or substrate material. Depending on the design, the thin layers can be applied below (bottom gate) or above (top gate) the semiconducting or insulating layer in the arrangement.

The electronic component preferably has an insulating layer which consists of polymers (for example poly(4-vinylphenol), polymethyl methacrylate, polystyrene, polyimides or polycarbonate) or ceramics (for example silicon dioxide, silicon nitride, aluminium oxide, gallium oxide, neodymium oxide, magnesium oxide, hafnium oxide, zirconium oxide).

The electronic component preferably has a semiconducting layer which consists of a semiconducting organic compound (for example polythiophene, oligothiophene or polytriarylamine) or ceramics (for example zinc oxide, indium gallium zinc oxide (IGZO) or zinc tin oxide (ZTO)).

The electronic component preferably has source and drain electrodes comprising a highly n-doped silicon thin layer, conductive polymers (for example polypyrrole-polyaminobenzenesulfonic acid or polyethylenedioxythiophene-polystyrenesulfonic acid (PEDOT-PSS)), conductive ceramics (for example indium tin oxide (ITO) or Al-, Ga- or In-doped tin oxide (AZO, GZO, IZO) and F- or Sb-doped tin oxide (FTO, ATO)) or metals (for example gold, silver, titanium, zinc). Depending on the design, the electrodes (preferably designed in accordance with the invention as thin layers) can be arranged below (bottom contact) or above (top contact) the semiconducting or insulating layer in the arrangement (see FIGS. 8a and b).

In the preferred embodiment mentioned above, the gate, insulator and semiconductor can be applied in an unstructured manner by means of spin coating or dip coating or deposition techniques from the gaseous or liquid phase. Furthermore, the gate, insulator, semiconductor and electrodes can be applied in a structured manner by means of flexographic/gravure printing, ink-jet printing or deposition techniques from the gaseous or liquid phase. Preference is given in accordance with the invention to printing processes.

The present invention furthermore relates to a process for the production of electronic structures having an aluminium, gallium, neodymium, ruthenium, magnesium, hafnium, zirconium, indium and/or tin oxide layer or surface or a mixture thereof, characterised in that
a) precursor solutions comprising the organometallic aluminium, gallium, neodymium, ruthenium, magnesium, hafnium, zirconium, indium and/or tin complex according to the invention or a mixture thereof are applied to a substrate in either one or more layers corresponding to the electronic structure to be achieved, by dip coating, spin coating or ink-jet printing or flexographic/gravure printing,
b) heating or drying of the applied precursor layer in air or an oxygen atmosphere with formation of an aluminium, gallium, neodymium, ruthenium, magnesium, hafnium, zirconium, indium, tin or indium tin oxide layer or surface,
c) finally, the applied electronic structure can be sealed by means of an insulating layer and is provided with contacts and completed.

By means of this process, both electronic components and also the compounds of individual components in integrated circuits are produced.

The following examples are intended to illustrate the present invention. However, they should in no way be regarded as limiting. All compounds or components which can be used in the compositions are either known and commercially available or can be synthesised by known methods.

EXAMPLE 1

Preparation of the Magnesium Oxide Precursor bis-[2-(methoxyimino)propanoato]magnesium Potassium hydrogencarbonate (12.02 g, 120 mmol) is added in small portions with stirring to a solution of sodium pyruvate (6.60 g, 60 mmol) and methoxylamine hydrochloride (5.01 g, 60 mmol) in 100 ml of water. When the visible evolution of gas is complete, the mixture is stirred for a further 30 minutes. Magnesium nitrate hexahydrate (7.69 g, 30 mmol) is subsequently added, and the mixture is stirred for a further one hour. The clear solution is concentrated to half the volume in a rotary evaporator and cooled to about 5 degrees. The white precipitate that has formed is filtered off and recrystallised from hot water. Yield 2.60 g (34.8%). The compound obtained in this way can be characterised by IR and NMR spectroscopy.

EXAMPLE 2

Alkali Metal-Free Preparation of the Magnesium Oxide Precursor bis[2-(methoxyimino)propanoato]magnesium Alternatively, the following reaction procedure is possible.
Hydromagnesite (20.0 g) is added in portions to a solution of pyruvic acid (10.56 g, 120 mmol) and methoxylamine hydrochloride (10.04 g, 120 mmol) in 100 ml of water. When the visible evolution of gas is complete, the mixture is stirred for one hour, and unreacted hydromagnesite is filtered off. The clear solution is concentrated to half the volume in a rotary evaporator and cooled to about 5 degrees. The white precipitate that has formed is filtered off and recrystallised from hot water. Yield 6.50 g (43.5%). The compound obtained in this way can be characterised by IR and NMR spectroscopy.

EXAMPLE 3

Production of Undoped Magnesium Oxide Layers from the Magnesium Precursor Having Insulator Properties (from Example 1 or 2)

The magnesium oximate prepared in accordance with Example 1 or 2 is applied to a glass, ceramic or polymer substrate by means of spin coating (or dip coating or also ink-jet printing). The coating is subsequently heated at temperatures above 210° C. in air for 10 minutes. The magnesium oxide films obtained in this way exhibit a uniform, crack-free, non-porous surface morphology. Depending on the calcination temperature, the layers consist of amorphous or nanocrystalline material. The layers have insulator properties.

EXAMPLE 4

Preparation of the Zirconium Dioxide Precursor Zirconium hydroxo[2-(methoxyimino)propanoate]

Sodium hydrogencarbonate (7.56 g, 90 mmol) is added in small portions with stirring to a solution of sodium pyruvate (9.90 g, 90 mmol) and methoxylamine hydrochloride (7.53 g, 90 mmol) in 100 ml of water. When the visible evolution of gas is complete, the mixture is stirred for a further 30 minutes. The mixture is subsequently evaporated to complete dryness in a rotary evaporator. A solution of zirconium tetrachloride (5.24 g, 22.5 mmol) in 125 ml of tetrahydrofuran is added to the white powder obtained in this way, and the mixture is stirred for 2 hours. The solution is filtered and evaporated to dryness in a rotary evaporator. The residue is taken up in 100 ml of dichloromethane, and the suspension obtained in this way is re-filtered. The product is subsequently precipitated from the filtrate using copious n-hexane, filtered off and dried in a desiccator. Yield 3.50 g. The compound obtained in this way can be characterised by IR and NMR spectroscopy.

EXAMPLE 5

Production of Zirconium Oxide Layers from the Zirconium Dioxide Precursor

The zirconium oximate prepared in accordance with Example 4 is applied to a glass, ceramic or polymer substrate by means of spin coating (or dip coating or also ink-jet printing). The coating is subsequently heated at temperatures above 200° C. in air for 10 minutes or irradiated with UV at 150 mW/cm$^2$ for 15 minutes. The zirconium oxide films obtained in this way exhibit a uniform, crack-free, non-porous surface morphology. Depending on the calcination temperature, the layers consist of amorphous or nano-crystalline material. The layers have insulator properties.

EXAMPLE 6

Preparation of the Hafnium Dioxide Precursor Hafnium hydroxo[2-(methoxyimino)propanoate]

Sodium hydrogencarbonate (7.56 g, 90 mmol) is added in small portions with stirring to a solution of sodium pyruvate (9.90 g, 90 mmol) and methoxylamine hydrochloride (7.53 g, 90 mmol) in 100 ml of water. When the visible evolution of gas is complete, the mixture is stirred for a further 30 minutes. The mixture is subsequently evaporated to complete dryness in a rotary evaporator. A solution of hafnium tetrachloride (7.21 g, 22.5 mmol) in 125 ml of tetrahydrofuran is added to the white powder obtained in this way, and the mixture is stirred for 2 hours. The solution is filtered and evaporated to dryness in a rotary evaporator. The residue is taken up in 100 ml of dichloromethane, and the suspension obtained in this way is re-filtered. The product is subsequently precipitated from the filtrate using copious n-hexane, filtered off and dried in a desiccator. Yield 4.75 g. The compound obtained in this way can be characterised by IR and NMR spectroscopy.

EXAMPLE 7

Production of Hafnium Oxide Layers Having Insulator Properties

The hafnium oximate prepared in accordance with Example 6 is applied to a glass, ceramic or polymer substrate by means of spin coating (or dip coating or also ink-jet printing). The coating is subsequently heated at temperatures above 200° C. in air for 10 minutes or irradiated with UV at 150 mW/cm$^2$ for 15 minutes. The hafnium oxide films obtained in this way exhibit a uniform, crack-free, non-porous surface morphology. Depending on the calcination temperature, the layers consist of amorphous or nano-crystalline material. The layers have insulator properties.

EXAMPLE 8

Preparation of the Aluminium Oxide Precursor tris-[2-(methoxyimino)propanoato]aluminium Sodium hydrogencarbonate (1.68 g, 20 mmol) is added in small portions with stirring to a solution of sodium pyruvate (2.20 g, 20 mmol) and methoxylamine hydrochloride (1.67 g, 20 mmol) in 50 ml of water. When the visible evolution of gas is complete, the mixture is stirred for a further 30 minutes. The mixture is subsequently evaporated to complete dryness in a rotary evaporator. A solution of aluminium nitrate nonahydrate (2.50 g, 6.6 mmol) in 125 ml of methanol is added to the white powder obtained in this way, and the mixture is stirred for 2 hours. The solution is filtered and evaporated to dryness in a rotary evaporator. The residue is taken up in 50 ml of dichloromethane, and the suspension obtained in this way is re-filtered. The product is subsequently precipitated from the filtrate using copious n-hexane, filtered off and dried in a desiccator. Yield 1.12 g (45.30%). The compound obtained in this way can be characterised by IR and NMR spectroscopy.

EXAMPLE 9

Production of Aluminium Oxide Layers Having Insulator Properties

The aluminium oximate prepared in accordance with Example 8 is applied to a glass, ceramic or polymer substrate by means of spin coating (or dip coating or also ink-jet printing). The coating is subsequently heated at temperatures above 200° C. in air for 10 minutes or irradiated with UV at 150 mW/cm$^2$ for 15 minutes. The aluminium oxide films obtained in this way exhibit a uniform, crack-free, non-porous surface morphology. Depending on the calcination temperature, the layers consist of nanocrystalline material. The layers have insulator properties.

EXAMPLE 10

Preparation of the Gallium Oxide Precursor Tris-[2-(methoxyimino)propanoato]gallium Sodium hydrogencarbonate (1.68 g, 20 mmol) is added in small portions with stirring to a solution of sodium pyruvate (2.20 g, 20 mmol) and methoxylamine hydrochloride (1.67 g, 20 mmol) in 50 ml of water. When the visible evolution of gas is complete, the mixture is stirred for a further 30 minutes. The mixture is subsequently evaporated to complete dryness in a rotary evaporator. A solution of gallium nitrate hexahydrate (2.40 g, 6.6 mmol) in 125 ml of methanol is added to the white powder obtained in this way, and the mixture is stirred for 2 hours. The solution is filtered and evaporated to dryness in a rotary evaporator. The residue is taken up in 100 ml of dichloromethane, and the suspension obtained in this way is re-filtered. The product is subsequently precipitated from the filtrate using copious n-hexane, filtered off and dried in a desiccator. Yield 0.96 g (34.82%). The compound obtained in this way can be characterised by IR and NMR spectroscopy.

EXAMPLE 11

Production of Gallium Oxide Layers Having Insulator Properties

The gallium oximate prepared in accordance with Example 10 is applied to a glass, ceramic or polymer substrate by means of spin coating (or dip coating or also ink-jet printing). The coating is subsequently heated at temperatures above 200° C. in air for 10 minutes or irradiated with UV at 150 mW/cm$^2$ for 15 minutes. The gallium oxide films obtained in this way exhibit a uniform, crack-free, non-porous surface morphology. Depending on the calcination temperature, the layers consist of nanocrystalline material. The layers have insulator properties.

EXAMPLE 12

Preparation of the Neodymium Oxide Precursor tris-[2-(methoxyimino)propanoato]neodymium Sodium hydrogencarbonate (1.68 g, 20 mmol) is added in small portions with stirring to a solution of sodium pyruvate (2.20 g, 20 mmol) and methoxylamine hydrochloride (1.67 g, 20 mmol) in 50 ml of water. When the visible evolution of gas is complete, the mixture is stirred for a further 30 minutes. The mixture is subsequently evaporated to complete dryness in a rotary evaporator. A solution of anhydrous neodymium trichloride (1.65 g, 6.6 mmol) in 125 ml of methanol is added to the white powder obtained in this way, and the mixture is stirred for 2 hours. The solution is filtered and evaporated to dryness in a rotary evaporator. The residue is taken up in 100 ml of dichloromethane, and the suspension obtained in this way is re-filtered. The product is subsequently precipitated from the filtrate using copious n-hexane, filtered off and dried in a desiccator. Yield 1.55 g (47.83%). The compound obtained in this way can be characterised by IR and NMR spectroscopy.

EXAMPLE 13

Production of Neodymium Oxide Layers Having Insulator Properties

The neodymium oximate prepared in accordance with Example 12 is applied to a glass, ceramic or polymer substrate by means of spin coating (or dip coating or also ink-jet printing). The coating is subsequently heated at temperatures above 200° C. in air for 10 minutes or irradiated with UV at 150 mW/cm$^2$ for 15 minutes. The neodymium oxide films obtained in this way exhibit a uniform, crack-free, non-porous surface morphology. or nano-crystalline material. The layers have insulator properties.

EXAMPLE 14

Preparation of the Ruthenium Oxide Precursor tris[2-(methoxyimino)propanoato]ruthenium Sodium hydrogencarbonate (1.68 g, 20 mmol) is added in small portions with stirring to a solution of sodium pyruvate (2.20 g, 20 mmol) and methoxylamine hydrochloride (1.67 g, 20 mmol) in 50 ml of water. When the visible evolution of gas is complete, the mixture is stirred for a further 30 minutes. The mixture is subsequently evaporated to complete dryness in a rotary evaporator. A solution of ruthenium trichloride hexahydrate (2.08 g, 6.6 mmol) in 125 ml of methanol is added to the white powder obtained in this way, and the mixture is stirred for 2 hours. The solution is filtered and evaporated to dryness in a rotary evaporator. The residue is taken up in 100 ml of dichloromethane, and the suspension obtained in this way is re-filtered. The product is subsequently precipitated from the filtrate using copious toluene, filtered off and dried in a desiccator. Yield 1.34 g (45.33%). The compound obtained in this way can be characterised by IR and NMR spectroscopy.

EXAMPLE 15

Production of Ruthenium Oxide Layers

The ruthenium oximate prepared in accordance with Example 14 is applied to a glass, ceramic or polymer substrate by means of spin coating (or dip coating or also ink-jet printing). The coating is subsequently heated at temperatures above 200° C. in air for 10 minutes or irradiated with UV at 150 mW/cm$^2$ for 15 minutes. The ruthenium oxide films obtained in this way exhibit a uniform, crack-free, non-porous surface morphology. Depending on the calcination temperature, the layers consist of nanocrystalline material.

EXAMPLE 16

Production of Dielectric Layers

The example shows the production of a dielectric layer. A layer of zirconium oxide is applied to a conductive highly n-doped silicon wafer by spin coating or printing and formed by subsequent calcination at 200° C. for 10 minutes or UV irradiation at 150 mW/cm$^2$ for 15 minutes. After application of a counter-electrode, the value of the breakdown voltage for the dielectric layer can be determined as 1 MV/cm.

EXAMPLE 17

Production of Thin-Film Transistors

Figure 1:
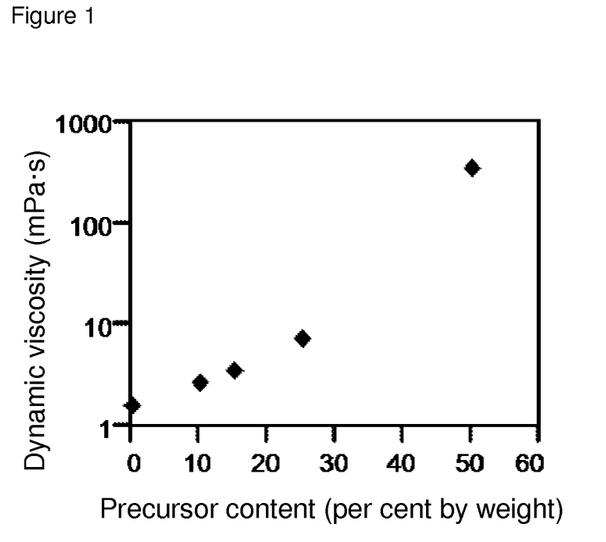
FIG. 1: shows the dependence of the dynamic viscosity on the precursor content for solutions of hafnium hydroxo[2-(methoxyimino)propanoate] in methoxyethanol. The measurement was carried out under standard environmental conditions (DIN 50 014-23).
Figure 2:
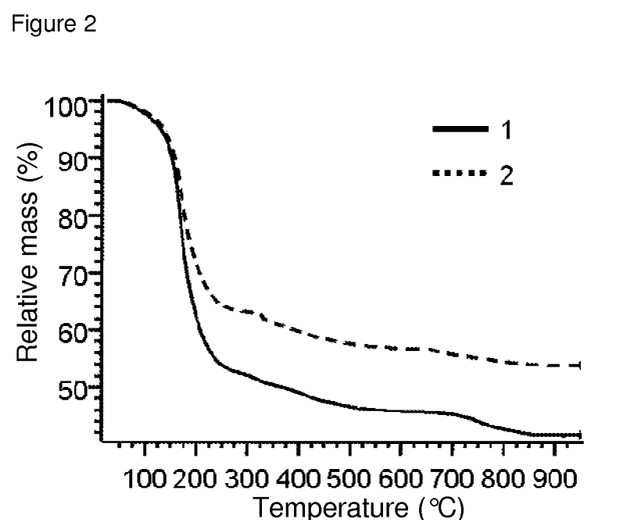
FIG. 2: shows a thermogravimetric analysis of zirconium and hafnium hydroxo[2-(methoxyimino)propanoate] in oxygen (1=curve for zirconium complex, 2=curve for hafnium complex). The decrease in the relative mass as a function of the temperature allows a conclusion to be drawn on the requisite reaction temperatures.
Figure 3:
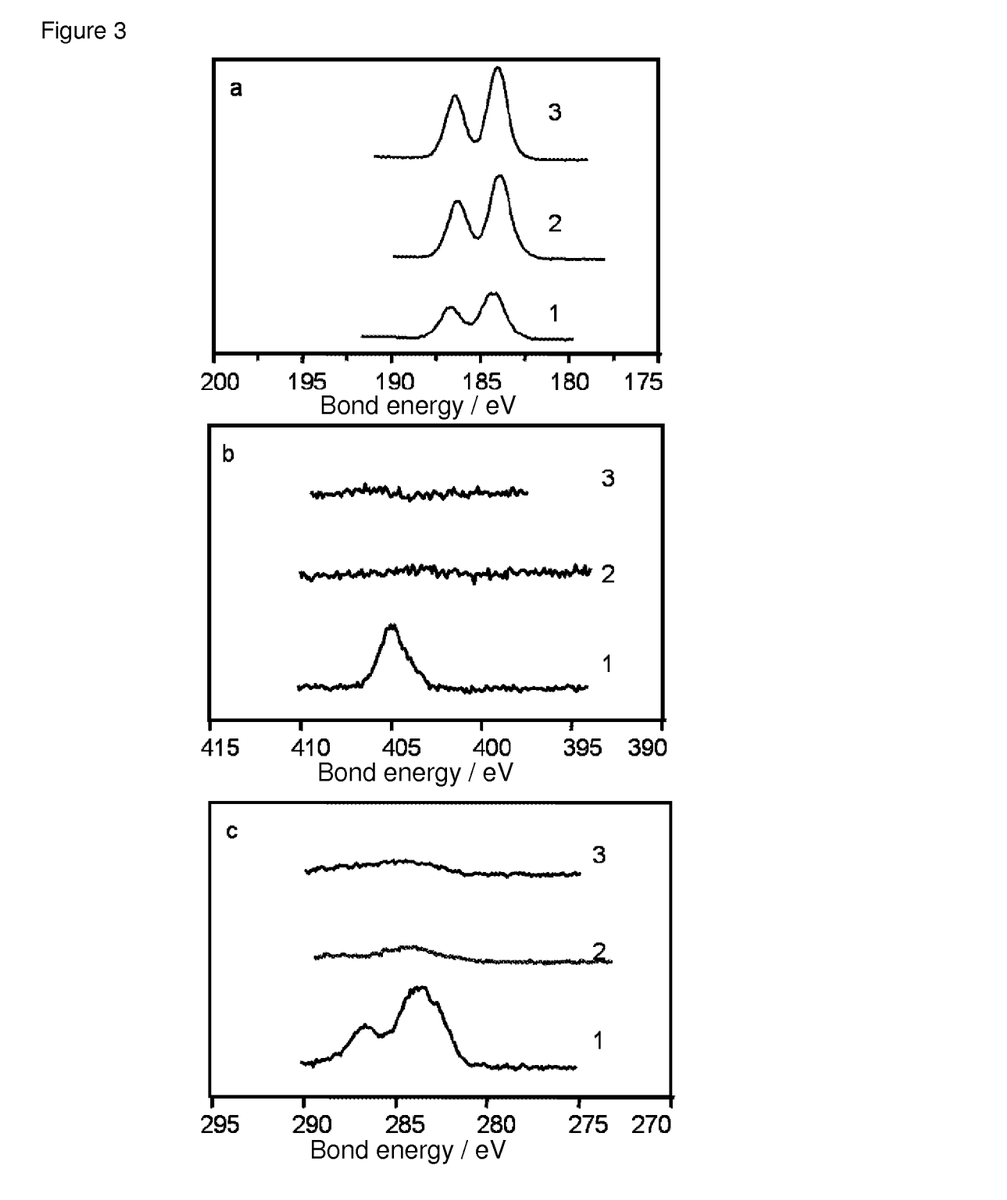
FIG. 3: shows an analysis by means of X-ray photon spectroscopy (XPS) of the films according to the invention comprising zirconium oximate in 2-methoxyethanol/2-butanol by spin coating on silicon substrates and processing at various temperatures for 30 minutes in each case.
Figure 4:
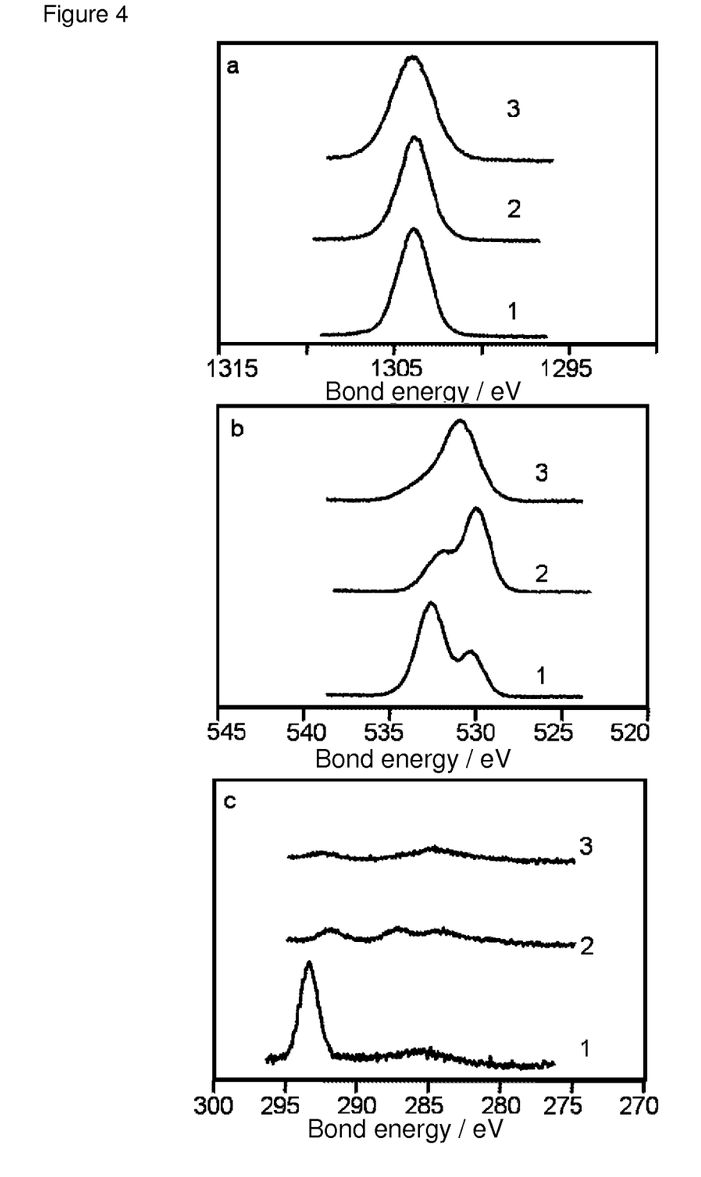
FIG. 4: shows an analysis by means of X-ray photon spectroscopy (XPS) of the films according to the invention comprising magnesium oximate in 2-methoxyethanol by spin coating on silicon substrates and processing at various temperatures for 30 minutes in each case.
Figure 5:
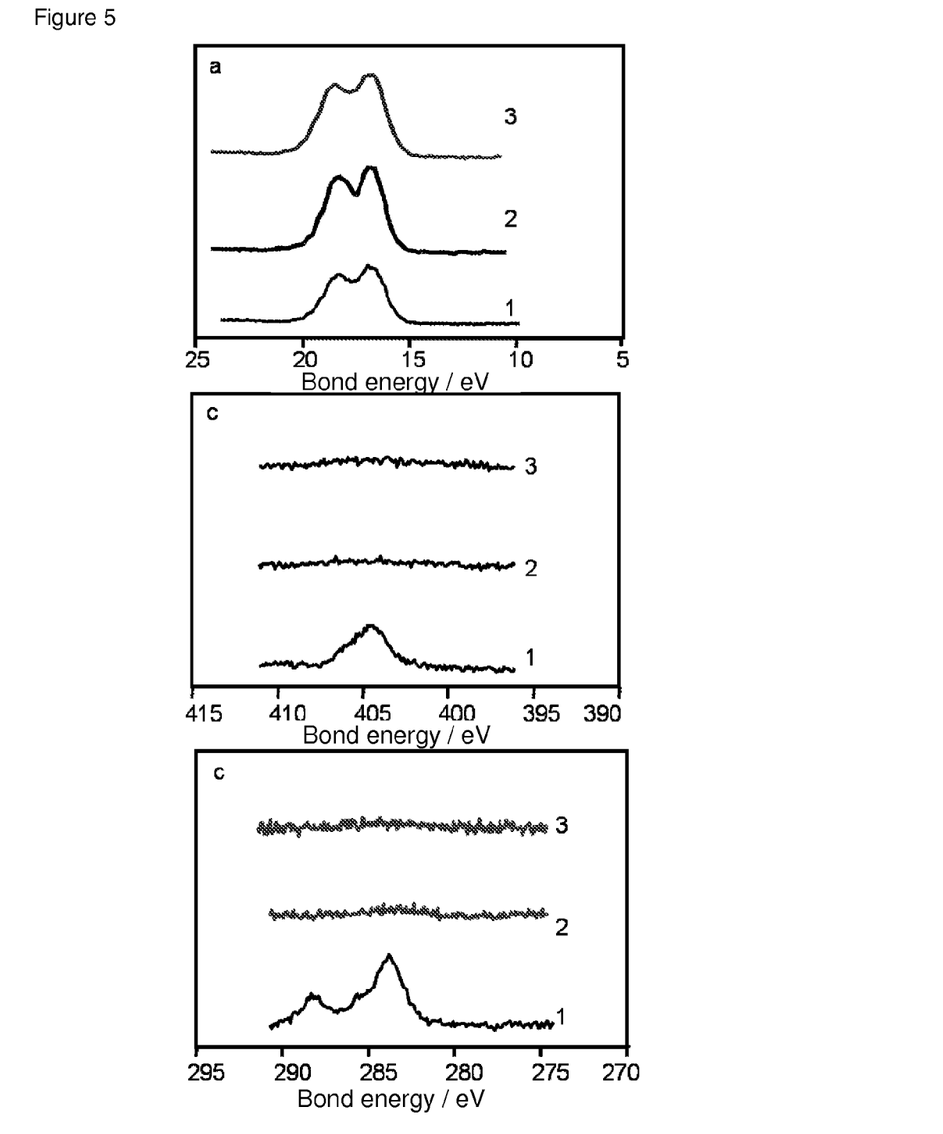
FIG. 5: shows an analysis by means of X-ray photon spectroscopy (XPS) of the films according to the invention comprising hafnium oximate in 2-methoxyethanol/2-butanol by spin coating on silicon substrates and processing at various temperatures for 30 minutes in each case.
Figure 6:
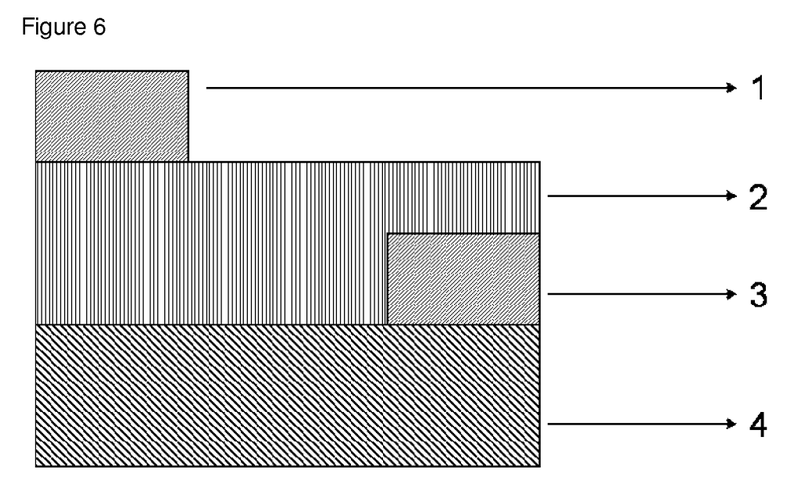
FIG. 6: shows a diagrammatic representation of the structure of a dielectric layer according to the invention. (1=conductor—gold or aluminium, 2=dielectric—zirconium oxide, 3=conductor—gold or aluminium, 4=substrate/insulator—glass).
Figure 7:
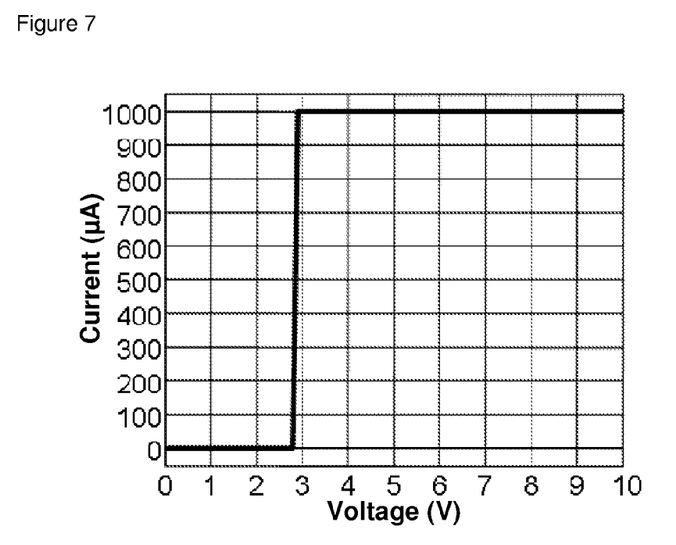
FIG. 7: shows a current/voltage curve for determination of the breakdown voltage in the component from FIG. 6.
Figure 8A:
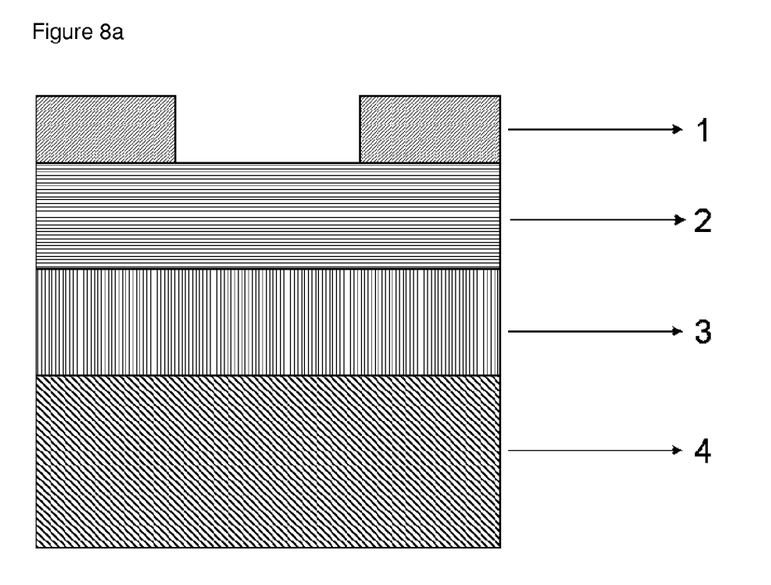
FIG. 8a: shows a diagrammatic representation of the structure of a thin-film field-effect transistor (1=conductor (drain and source), 2=semiconductor, 3=dielectric, 4=conductor (gate)).
Figure 8B:
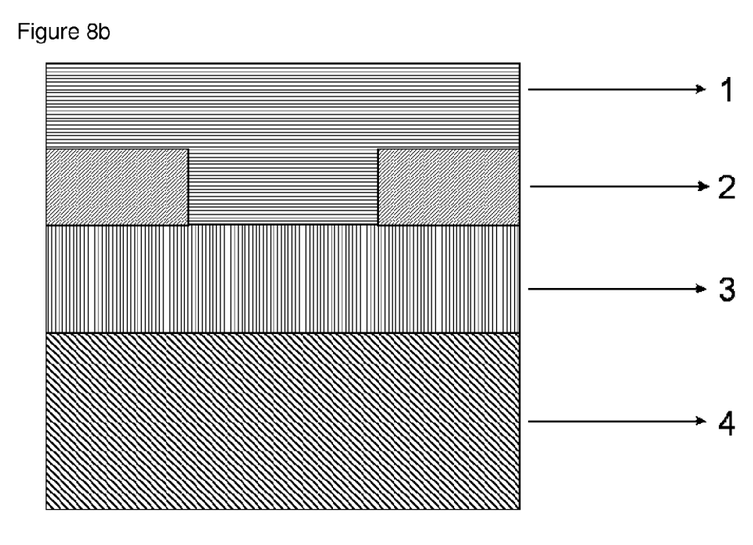
FIG. 8b: shows a diagrammatic representation of the structure of a thin-film field-effect transistor (1=semiconductor, 2=conductor (drain and source), 3=dielectric, 4=conductor (gate)).

The example shows a field-effect transistor (FET) in accordance with FIGS. 8a and 8b. The component consists of a highly n-doped silicon wafer to which the dielectric layer has been applied. A semiconducting layer is then produced, followed by a metal electrode structure, which is produced by vapour deposition of the metal or printing of a metal ink (FIG. 8a). Alternatively, the electrode structure can be produced first followed by the application of the semiconductor layer (FIG. 8b).

EXAMPLE 18

Preparation of the Indium Oxide Precursor Tris-[2-(methoxyimino)propanoato]indium Sodium hydrogencarbonate (1.68 g, 20 mmol) is added in small portions with stirring to a solution of sodium pyruvate (2.20 g, 20 mmol) and methoxylamine hydrochloride (1.67 g, 20 mmol) in 50 ml of water. When the visible evolution of gas is complete, the mixture is stirred for a further 30 minutes. The mixture is subsequently evaporated to complete dryness in a rotary evaporator. A solution of anhydrous indium chloride (1.95 g, 6.6 mmol) in 125 ml of methanol is added to the white powder obtained in this way, and the mixture is stirred for 2 hours. The solution is filtered and evaporated to dryness in a rotary evaporator. The residue is taken up in 100 ml of dichloromethane, and the suspension obtained in this way is re-filtered. The product is subsequently precipitated from the filtrate using copious n-hexane, filtered off and dried in a desiccator. Yield 1.80 g (58.9%). The compound obtained in this way can be characterised by IR and NMR spectroscopy.

EXAMPLE 19

Preparation of the tin oxide precursor tin hydroxo[2-(methoxyimino)propanoate]

Sodium hydrogencarbonate (7.56 g, 90 mmol) is added in small portions with stirring to a solution of sodium pyruvate (9.90 g, 90 mmol) and methoxylamine hydrochloride (7.53 g, 90 mmol) in 100 ml of water. When the visible evolution of gas is complete, the mixture is stirred for a further 30 minutes. The mixture is subsequently evaporated to complete dryness in a rotary evaporator. A solution of anhydrous tin chloride pentahydrate (7.88 g, 22.5 mmol) in 250 ml of methanol is added to the white powder obtained in this way, and the mixture is stirred for 2 hours. The solution is filtered and evaporated to dryness in a rotary evaporator. The residue is taken up in 100 ml of acetone or dimethoxyethane, and the suspension obtained in this way is re-filtered. The product is subsequently precipitated from the filtrate using copious diethyl ether, filtered off and dried in a desiccator. Yield 3.7 g. The compound obtained in this way can be characterised by IR and NMR spectroscopy.

EXAMPLE 20

Production of Electrically Conductive Layers of Indium Tin Oxide (ITO)

The indium and tin oximates prepared in accordance with Examples 18 and 19 are dissolved together in the molar ratio 90:10 and applied to a glass, ceramic or polymer substrate by means of spin coating (or dip coating or also ink-jet printing). The coating is subsequently heated at temperatures above 200° C. in air for 60 minutes or irradiated with UV at 150 mW/cm$^2$ for 1 hour. The indium tin oxide films obtained in this way exhibit a uniform, crack-free, non-porous surface morphology. Depending on the calcination temperature, the layers consist of amorphous or nanocrystalline material. The layers have electrical conductivity.

EXAMPLE 21

Production of Semiconducting Layers of Indium Gallium Zinc Oxide (IGZO)

The indium and/or gallium oximates prepared in accordance with Examples 10 and 18 and zinc oximates (accessible by the method of J. J. Schneider et al. Advanced Materials, 2008, 20, 3383-3387) are dissolved in a suitable molar ratio. Suitable molar ratios for the preparation of semiconducting phases are given in H. Hosono, Journal of Non-Crystalline Solids 2006, 352, 851-858; thus, for example, indium:gallium:zinc=1:1:1 or indium:zinc=2:3.

The solution obtained in this way is applied to a glass, ceramic or polymer substrate by means of spin coating (or dip coating or also ink-jet printing). The coating is subsequently heated at temperatures above 200° C. in air for 10 minutes or irradiated with UV at 150 mW/cm$^2$ for 15 minutes. The indium gallium zinc oxide films obtained in this way exhibit a uniform, crack-free, non-porous surface morphology. Depending on the calcination temperature, the layers consist of amorphous material. The layers have semiconducting properties.

EXAMPLE 22

Production of Semiconducting Layers of Zinc Tin Oxide (ZTO)

The tin oximates prepared in accordance with Example 19 and zinc oximates (accessible by the method of J. J. Schneider et al. Advanced Materials, 2008, 20, 3383-3387) are dissolved together in a suitable ratio. Tin contents Sn/(Sn+Zn) of 0 to 30 mole percent, for example, are suitable. The solution is applied to a glass, ceramic or polymer substrate by means of spin coating (or dip coating or also ink-jet printing). The coating is subsequently heated at temperatures above 200° C. in air for 10 minutes or irradiated with UV at 150 mW/cm$^2$ for 15 minutes. The zinc tin oxide films obtained in this way exhibit a uniform, crack-free, non-porous surface morphology. Depending on the calcination temperature, the layers consist of amorphous or nanocrystalline material. The layers have semiconducting properties.

EXAMPLES 23 TO 26

Description of Various Coating Processes

In all cases, solutions of 10-20 percent by weight of the precursor compounds are used. Suitable solvents are 2-methoxyethanol, 2-butanol, methanol, dimethylformamide or mixtures thereof.

The viscosity of the printing inks can be determined using a rheometer, for example MARS Rheometer from Haake. The determination is carried out under standard environmental conditions (DIN 50 014-23).

Dip coating: Drawing rate ~1 mm/sec. The substrates employed are 76×26 mm glass plates.

Spin coating: For spin coating, 150 μl of solution are applied to the substrate. The substrate used is 20×20 mm quartz or 15×15 mm silicon (with gold electrodes for the production of the FETs). The parameters selected for duration and speed are 10 s at a preliminary speed of 1000 rpm and 20 s at a final speed of 2000 rpm.

Ink-jet printing: The printing process can be carried out using a Dimatix DMP 2831 printer from Dimatix. The printing ink used is a solution of 10 percent by weight of the hafnium oxide precursor hafnium hydroxo[2-(methoxyimino)propanoate] in diethylene glycol monoethyl ether, which is introduced using a syringe filter having a pore size of 0.2 μm. Films can be printed on substrates, such as glass, with indium tin oxide coating (Merck) and converted into the ceramic by subsequent UV irradiation (Fe-doped Hg lamp; irradiation duration: 4 min at 400 mW/cm$^2$).

Flexographic printing: The printing process can be carried out using an IGT F1 unit from IGT Testing Systems.

The printing ink used is a solution of 10 percent by weight of the hafnium oxide precursor hafnium hydroxo[2-(methoxyimino)propanoate] in methoxyethanol. 1 ml of solution is applied manually to the contact zone.

The following printing parameters are selected for knife-coating sheet/anilox roll:

anilox roll/plate cylinder contact pressure 10 N
plate cylinder/counterpressure cylinder contact pressure 10 N
printing speed 0.8 m/s
printing plate: full-tone surface, 90% area coverage
anilox roll uptake volume 20 ml/m$^2$ Full-area printing can be achieved on substrates such as silicon or quartz. The precursor can subsequently be converted into the ceramic by UV irradiation (Fe-doped Hg lamp; irradiation duration: 7 min at 400 mW/cm²).

BRIEF DESCRIPTION OF DRAWINGS

The invention will be explained in greater detail below with reference to a number of illustrative embodiments (see FIGS. 1 to 8b).

(a=Zr3d signal. b=N1s signal. c=C1s signal. 1=without further processing. 2=processing at 200° C. 3=processing at 250° C.)

The XPS spectra allow a conclusion to be drawn on the elements present in the sample and the oxidation state and on the mixing ratio. It can thus be shown that zirconium oxide is present in the films after processing.

In the case of some measurements, the surface was cleaned in the measurement chamber by sputtering.

(a=Mg1s signal. b=O1s signal. c=C1s signal. 1=processing at 210° C.+sputtering. 2=processing at 450° C. 3=processing at 450° C.+sputtering.) The XPS spectra allow a conclusion to be drawn on the elements present in the sample and the oxidation state and on the mixing ratio. It can thus be shown that magnesium oxide is present in the films after processing.

(a=Hf4f signal. b=N1s signal. c=C1s signal. 1=without processing. 2=processing at 200° C. 3=processing at 250° C.)

The XPS spectra allow a conclusion to be drawn on the elements present in the sample and the oxidation state and on the mixing ratio. It can thus be shown that hafnium oxide is present in the films after processing.

The current/voltage curve shows the typical shape for a dielectric; the breakdown voltage can be determined therefrom as important parameter of the material.

The component has the electrodes in the top-contact arrangement.

The component has the electrodes in the bottom-contact arrangement.

The invention claimed is:

1. A precursor for coating an electronic component, comprising an organometallic aluminum, gallium, neodymium, ruthenium, magnesium, hafnium, zirconium, indium and/or tin complex or a mixture thereof, which contains at least one oximate ligand.

2. A precursor according to claim 1, wherein the ligand is a 2-(methoxyimino)alkanoate, 2-(ethoxyimino)alkanoate or 2-(hydroxy-imino)alkanoate.

3. A precursor according to claim 1, which is printable and is in the form of a printing ink or printing paste in a printed field-effect transistor.

4. A printed electronic component which has the following thin layers:
- a solid or flexible conductive substrate or an insulating substrate having a conductive layer;
- an insulator comprising an aluminum, gallium, neodymium, magnesium, hafnium or zirconium oxide obtainable from a corresponding precursor according to claim 1;
- at least one electrode;
- a semiconductor.

5. A printed electronic component which has the following thin layers:
- a solid or flexible conductive substrate or an insulating substrate having a conductive layer comprising an indium tin oxide obtainable from a corresponding precursor according to claim 1;
- an insulator;
- at least one electrode;
- a semiconductor.

6. A printed electronic component which has the following thin layers:
- a solid or flexible conductive substrate or an insulating substrate having a conductive layer;
- an insulator;
- at least one electrode;
- a semiconductor comprising an indium gallium zinc oxide or a zinc tin oxide, obtainable from a corresponding precursor according to claim 1.

7. A printed electronic component according to claim 4, wherein the substrate is a solid substrate, or a flexible substrate.

8. A process for preparing a precursor for coating an electronic component, comprising an organometallic aluminum, gallium, neodymium, ruthenium, magnesium, hafnium, zirconium, indium and/or tin complex or a mixture thereof, which contains at least one oximate ligand, said process comprising reacting at least one oxycarboxylic acid with at least one hydroxylamine or alkylhydroxylamine in the presence of a base, and subsequently adding an inorganic aluminum, gallium, neodymium, ruthenium, magnesium, hafnium, zirconium, indium and/or tin salt or a mixture thereof.

9. A process according to claim 8, wherein the oxocarboxylic acid is oxoacetic acid, oxopropionic acid or oxobutyric acid.

10. A process for preparing an electronic structure having an aluminum, gallium, neodymium, ruthenium, magnesium, hafnium, zirconium, indium and/or tin oxide layer or surface or a mixture thereof, comprising
   a. applying a precursor comprising organometallic aluminum, magnesium, gallium, neodymium, ruthenium, hafnium, zirconium, indium and/or tin complex or a mixture thereof according to claim 1, which precursor is in a solution, to a substrate in either one or more layers corresponding to the electronic structure to be achieved by dip coating, spin coating or ink-jet printing or flexographic/gravure printing,
   b. heating or drying the applied precursor layer in air or an oxygen atmosphere with formation of an aluminum, gallium, neodymium, ruthenium, magnesium, hafnium, zirconium, indium, and/or tin oxide layer or surface or a mixture thereof,
   c. finally, the applied electronic structure is optionally sealed by an insulating layer and is provided with contacts.

11. A process according to claim 10, wherein the temperature during heating is T≥80° C.

12. A process according to claim 10, wherein the heating or drying is carried out by irradiation with UV light having a wavelength <400 nm.

13. A process according to claim 10, wherein the aluminum oxide, gallium oxide, neodymium oxide, ruthenium oxide, magnesium oxide, hafnium oxide or zirconium oxide layers have a breakdown voltage of >0.1 MV/cm between two conductors.

14. A process according to claim 10, wherein an indium tin oxide layer is prepared, that has a specific resistance, determined by four-point measurement, of $<10^{-3}$ ohm·cm.

15. A process according to claim 10, wherein an indium gallium zinc oxide layer or a zinc tin oxide layer is prepared, that has a charge-carrier mobility of $>10^{-3}$ cm2/Vs.

16. A field-effect transistor comprising a functional layer prepared from a precursor for coating an electronic component, comprising an organometallic aluminum, gallium, neodymium, ruthenium, magnesium, hafnium, zirconium, indium and/or tin complex or a mixture thereof, which contains at least one oximate ligand.

17. A printed electronic component according to claim 4, wherein the substrate is a solid substrate selected from the group consisting of glass, ceramic, metal and plastic substrate, or is a flexible substrate selected from the group consisting of plastic film and metal foil.

18. A printed electronic component according to claim 5, wherein the substrate is a solid substrate, or a flexible substrate.

19. A printed electronic component according to claim 6, wherein the substrate is a solid substrate, or a flexible substrate.

20. A printed electronic component according to claim 5, wherein the substrate is a solid substrate selected from the group consisting of glass, ceramic, metal and plastic substrate, or is a flexible substrate selected from the group consisting of plastic film and metal foil.

21. A printed electronic component according to claim 6, wherein the substrate is a solid substrate selected from the group consisting of glass, ceramic, metal and plastic substrate, or is a flexible substrate selected from the group consisting of plastic film and metal foil.

* * * * *